US00PP19455P2

(12) United States Plant Patent
Danziger

(10) Patent No.: US PP19,455 P2
(45) Date of Patent: Nov. 18, 2008

(54) ***VERBENA* PLANT NAMED 'DANVER47'**

(50) Latin Name: *Verbena hybrida*
Varietal Denomination: DANVER47

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,649

(22) Filed: Jan. 11, 2008

(51) Int. Cl.
*A01H 5/00* (2006.01)

(52) U.S. Cl. ..... Plt./308

(58) Field of Classification Search ..... Plt./308
See application file for complete search history.

*Primary Examiner*—Annette H Para

(57) ABSTRACT

A new and distinct *Verbena* cultivar named 'DANVER47' is disclosed, characterized by having a distinctive magenta flower color, relatively large flower size and deeply incised foliage margins. The new variety is a *Verbena,* normally produced as an outdoor garden or container plant.

2 Drawing Sheets

Latin name of the genus and species: *Verbena hybrida.*
Variety denomination: 'DANVER47'.

BACKGROUND OF THE INVENTION

The new *Verbena* cultivar is a product of a planned breeding program conducted by the inventor, Gabriel Danziger, in Moshav Mishmar Hashiva, Israel. The objective of the breeding program was to produce new varieties of Verbena for commercial introduction.

The seed parent is the unpatented, proprietary seedling variety referred to as *Verbena* hybrida 'VE-5-1081.' The pollen parent is unknown as the new variety is the result of an open pollination in which the male parent cannot be identified.

The new variety was discovered in June 2006 by the inventor in a group of seedlings resulting from that crossing, in a commercial greenhouse in Moshav Mishmar Hashiva, Israel. Asexual reproduction of the new cultivar 'DANVER47' by vegetative cuttings was first performed at a commercial greenhouse in Moshav Mishmar Hashiva, Israel in October 2006. Subsequent propagation has shown that the unique features of this cultivar are stable and reproduced true to type on successive generations.

SUMMARY OF THE INVENTION

The cultivar 'DANVER47' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANVER47'. These characteristics in combination distinguish 'DANVER47' as a new and distinct *Verbena* cultivar:

1. Distinctive magenta flower color.
2. Relatively large flower size.
3. Deeply incised foliage margin.

Plants of the new cultivar 'DANVER47' are similar to plants of the female parent, *Verbena hybrida* 'VE-5-1018' in most horticultural characteristics, however, plants of the new cultivar 'DANVER47' have a much darker flower and a different shaped foliage. The female parent has incised foliage, whereas 'DANVER47' foliage is pinnate and broad.

COMMERCIAL COMPARISON

Plants of the new cultivar 'DANVER47' are best compared to the commercial variety *Verbena* 'Escapade Bright Eye,' U.S. patent unknown. Plants of 'DANVER47' are similar to plants of *Verbena* 'Escapade Bright Eye' in most horticultural characteristics, however, plants of the new variety have a completely different foliage margin, and a solid magenta colored flower, compared to the white eye and magenta of 'Escapade Bright Eye'.

BRIEF DESCRIPTION OF THE PHOTOGRAPH

Figure 1:
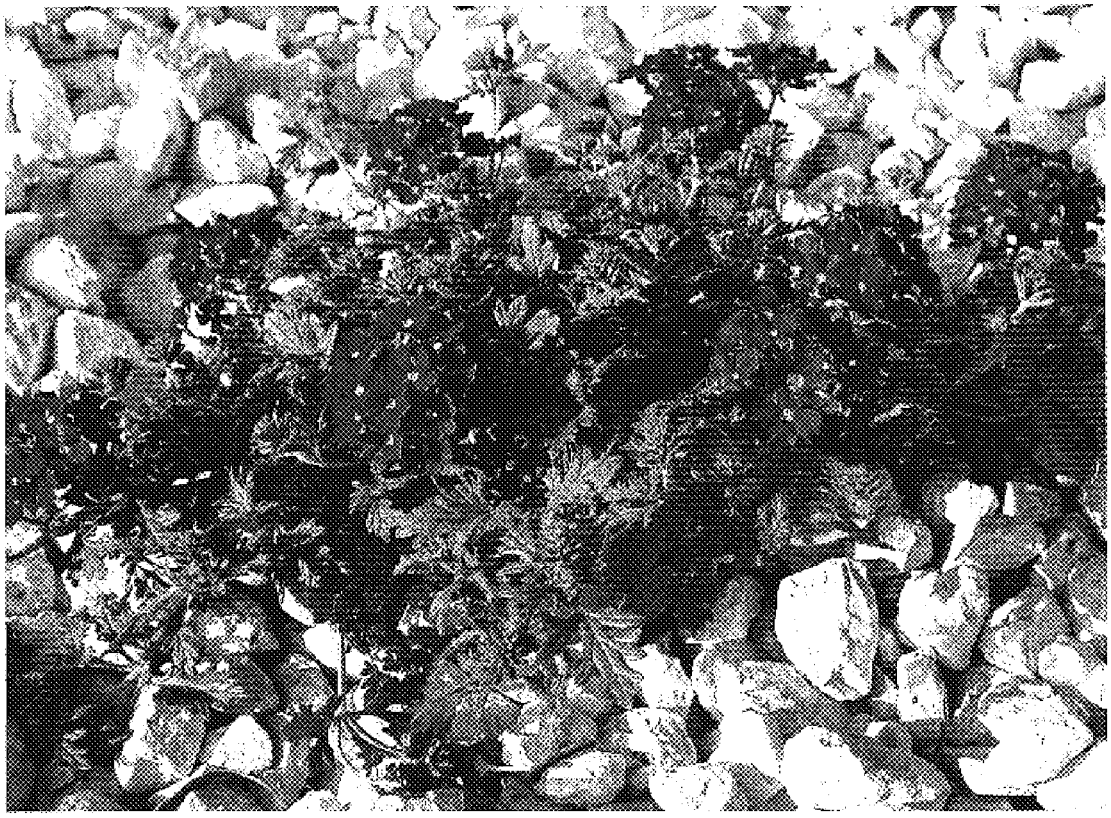

The accompanying photograph in FIG. 1 illustrates in full color a typical plant of 'DANVER47' grown in a greenhouse, in a 13 cm pot. Age of the plant photographed is approximately 5 weeks from a rooted cutting.

Figure 2:
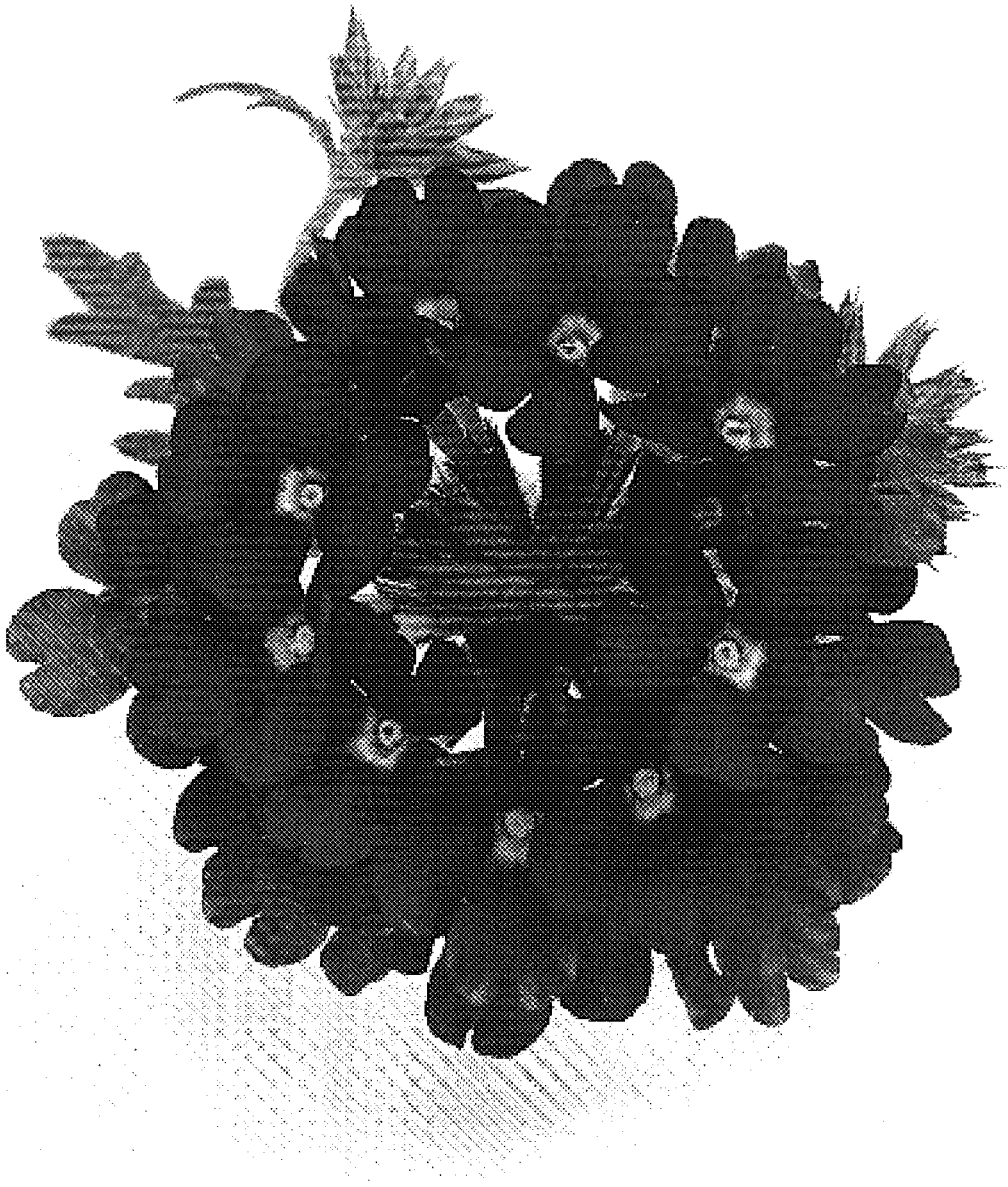

FIG. 2 illustrates in full color a close up of a typical bloom of 'DANVER47'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANVER47' plants grown in a greenhouse in Moshav Mishmar Hashiva, Israel. The growing temperature ranged from 20° C. to 28° C. The greenhouse in un-shaped, giving bright, normal sunlight conditions. Measurements and numerical values represent averages of typical plant types.

Botanical classification: *Verbena hybrida* cultivar 'DANVER47.'

PROPAGATION

Time to initiate roots: About 6 days at approximately 18–30° C.
Time to develop roots: About 14 days at approximately 18–30° C.
Root description: Fine, densely fibrous.

PLANT

Growth habit: Spreading.
Pot size of plant described: 12 cm.
Height: Approximately 10 cm.
Plant spread: Approximately 40 cm.
Growth rate: Moderate.
Branching characteristics: Highly branched.
Length of lateral branches: Approximately 30 to 40 cm.
Diameter of lateral branches: Approximately 0.2 cm.
Color of branches: Near RHS Green 143C.
Texture: Pubescent.
Internode length: Approximately 3.5 cm.
Age of plant described: Approximately 21 days from a rooted cutting.

FOLIAGE

Arrangement: Opposite.
Leaves per branch: Approximately 8.
Leaves:
*Size.*—Length: About 3.5 to 5.0 cm. Width: About 2.5 to 3.5 cm. Shape of leaf: Deltoid. Shape of apex: Acute. Shape of base: Acuminate. Texture: Puberulous. Aspect: 45° to stem. Margin type: Incised margin.
*Color.*—Young leaves: Upper surface: RHS Green 137B. Lower surface: RHS Green 138B. Mature leaves: Upper surface: RHS Green 137A. Lower surface: RHS Green 137D.
Petiole: Not Present
Veins:
*Venation pattern.*—Palmate.
*Color.*—Upper surface: RHS Green 143B. Lower surface: RHS Green 143C.

FLOWER

Bud: Described 2 days before anthesis.
*Shape.*—Quinquangular.
*Diameter.*—Approximately 0.1 cm.
*Length.*—Approximately 1 cm.
*Color.*—Near RHS Green 137B.
Natural flowering season: Summer in Israel.
Flower type: Zygomorphic, salverform.
Corolla:
*Petals/lobes.*—Number: 5. Length: 9 mm. Width: 8 mm. Shape: Similar to obcordate. Aspect: Upright. Margin: Entire. Texture: Smooth. Color: When opening: Upper surface: Red-Purple 61 B. Lower surface: Red-Purple 61A. Fully opened: Upper surface: Red-Purple 61A. Lower surface: Red-Purple 74A.
*Throat.*—Color: Yellow-Green 150D. Texture: Slightly pubescent.
*Tube color.*—Yellow-Green 150C.
Calyx:
*Form.*—Fused.
*Length.*—1 cm.
*Diameter.*—2 mm.
*Sepal shape.*—Quinquangular.
*Sepal margin.*—Entire.
*Sepal texture.*—Strigose.
*Sepal color.*—Upper surface: Yellow-green 147 B. Lower surface: Yellow-green 147 A.
Fragrance: None.

REPRODUCTIVE ORGANS

Stamens:
*Number (per flower).*—4.
*filament length.*—About 0.2 cm.
*Anthers.*—Shape: Oval. Length: About 0.1 cm. Color: RHS Green-Yellow 150 C.
Pollen:
*Color.*—RHS Yellow-Green 1D.
*Amount.*—Abundant.
Pistils:
*Quantity per flower.*—1.
*Length.*—About 0.15 cm.
*Styles.*—Length: About 0.14 cm. Color: Yellow-Green 1D.
*Stigma.*—Shape: Ovoid. Color: Near RHS Yellow-Green N144C.

OTHER CHARACTERISTICS

Disease resistance: Slightly better tolerance of powdery mildew than most commercial varieties.
Temperature tolerance: Tolerant to high temperatures above 30° C.
Seed and fruit production: Produces small amounts of seed.

What is claimed is:

1. A new and distinct cultivar of *Verbena* plant named 'DANVER47' as herein illustrated and described.

* * * * *

UNITED STATES PATENT AND TRADEMARK OFFICE

CERTIFICATE OF CORRECTION

PATENT NO. : PP 19,455 P2
APPLICATION NO. : 12/008649
DATED : November 18, 2008
INVENTOR(S) : Gabriel Danziger It is certified that error appears in the above-identified patent and that said Letters Patent is hereby corrected as shown below:

Plant Name is incorrect. The Plant Name in the patent is 'Danver47.'

The correct Plant Name is: 'Dandon47'

Correct for all sections of the patent which the plant name 'Danver47' is used, including:
Title of the Invention
Claim
Abstract
Specification Signed and Sealed this Twentieth Day of April, 2010

David J. Kappos

David J. Kappos
*Director of the United States Patent and Trademark Office*